United States Patent
Shinada et al.

(10) Patent No.: US 10,161,906 B2
(45) Date of Patent: Dec. 25, 2018

(54) DIELECTRIC BARRIER DISCHARGE IONIZATION DETECTOR AND METHOD FOR TUNING THE SAME

(71) Applicant: SHIMADZU CORPORATION, Kyoto-shi, Kyoto (JP)

(72) Inventors: Kei Shinada, Uji (JP); Shigeyoshi Horiike, Uji (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 506 days.

(21) Appl. No.: 14/611,516

(22) Filed: Feb. 2, 2015

(65) Prior Publication Data

US 2015/0253286 A1    Sep. 10, 2015

(30) Foreign Application Priority Data

Mar. 4, 2014    (JP) .................................. 2014-041205

(51) Int. Cl.
*G01N 27/68* (2006.01)
*G01N 33/00* (2006.01)
(Continued)

(52) U.S. Cl.
CPC ............. *G01N 27/68* (2013.01); *G01N 27/70* (2013.01); *G01N 30/64* (2013.01); *G01N 33/0027* (2013.01)

(58) Field of Classification Search
CPC ........ G01N 30/64; G01N 27/62; G01N 27/68; G01N 27/70; G01N 27/622; G01N 33/0027
See application file for complete search history.

(56) References Cited

U.S. PATENT DOCUMENTS 6,498,344 B1 * 12/2002 Littlejohn ............... H01J 41/18
250/283
2004/0232326 A1 * 11/2004 Guevremont ........ G01N 27/624
250/287
(Continued)

FOREIGN PATENT DOCUMENTS

CN    103293217 A    9/2013
JP    2010-60354 A    3/2010
(Continued)

OTHER PUBLICATIONS

Shinada et al., "Yuudentai Baria Houden Wo Ouyou-shita Gasu Kuromatogurafu-you Shinki Ionka Kenshutsuki No Kaihatsu", (Development of New Ionization Detector for Gas Chromatograph by Applying Dielectric Barrier Discharge), Shimadzu Hyouron (Shimadzu Review), Mar. 29, 2013, pp. 255-263, vol. 69, No. 3-4.
(Continued)

*Primary Examiner* — Son Le
*Assistant Examiner* — Dustin Dickinson
(74) *Attorney, Agent, or Firm* — Westerman, Hattori, Daniels & Adrian, LLP

(57) ABSTRACT

To widen the dynamic range of a dielectric barrier ionization detector (BID), an insertion length of a sample injection tube 16 into a second gas passage 11 is set so that a sample-gas ejection port 16a is located on the downstream side of a dilution gas from the upper edge of a collector electrode 14 at which a DC electric field concentrates. By this setting, although the detection sensitivity is lower than in the case where the sample-gas ejection port 16a is placed to maximize the detection sensitivity, the decrease in the detection sensitivity to high-concentration samples is reduced since absorption of light by the sample gas is alleviated. Consequently, the sample-concentration range with a linearly-changing sensitivity becomes wider than that of conventional BIDs. Although the detection sensitivity becomes (Continued)

lower than that of conventional BIDs, a detection sensitivity adequately higher than that of FIDs can be ensured.

9 Claims, 6 Drawing Sheets

(51) Int. Cl.
    *G01N 27/70*     (2006.01)
    *G01N 30/64*     (2006.01)

(56) References Cited

U.S. PATENT DOCUMENTS

2011/0316551 A1* 12/2011 Shinada ................. G01N 30/64
                                                                     324/464

2011/0316552 A1* 12/2011 Shinada ................. G01N 27/70
                                                                     324/464
2013/0221972 A1     8/2013   Uchiyama

FOREIGN PATENT DOCUMENTS

| JP | 2011-158357 A | 8/2011 | |
|---|---|---|---|
| WO | 2012/169419 A1 | 12/2012 | |
| WO | WO2012/169419 | * 12/2012 | ............. G01N 27/68 |

OTHER PUBLICATIONS

Forsyth, "Pulsed discharge detector: theory and applications", Journal of Chromatography A, 2004, pp. 63-68, vol. 1050.

Shinada et al., "Development of New Ionization Detector for Gas Chromatography by Applying Dielectric Barrier Discharge", Shimadzu Review, Dec. 14, 2012.

* cited by examiner

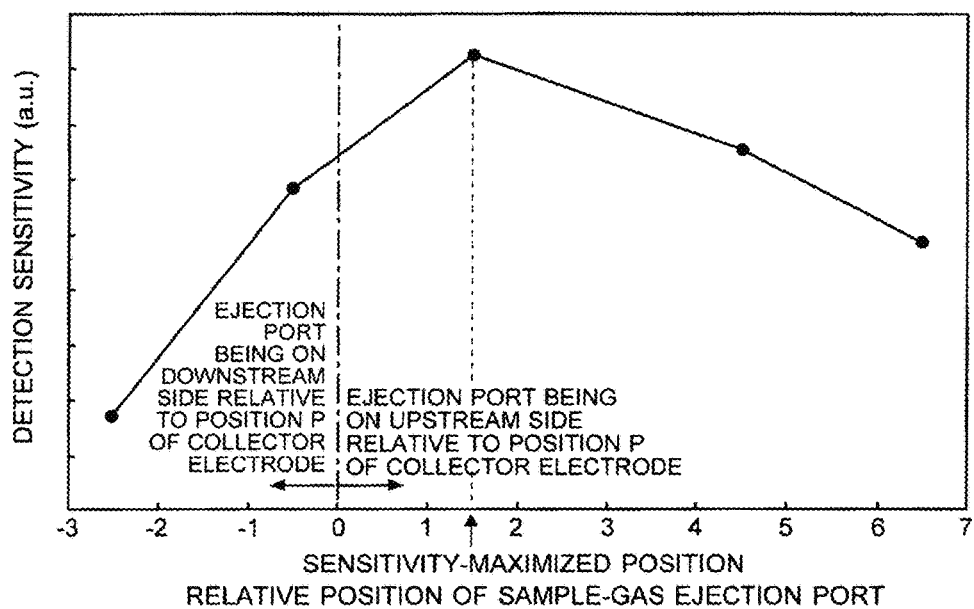
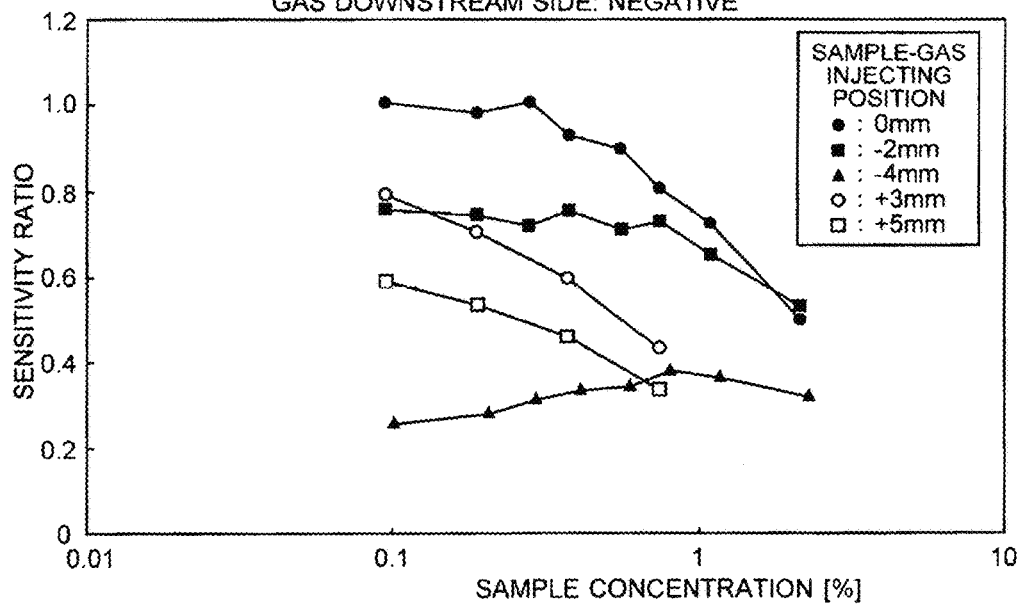

DIELECTRIC BARRIER DISCHARGE IONIZATION DETECTOR AND METHOD FOR TUNING THE SAME

TECHNICAL FIELD

The present invention relates to a dielectric barrier discharge ionization detector which is primarily suitable as a detector for a gas chromatograph (GC) as well as a method for tuning the detector.

BACKGROUND ART

As a detector for a gas chromatograph, various types of detectors have been put to practical use, such as a thermal conductivity detector (TCD), electron capture detector (ECD), flame ionization detector (FID), flame photometric detector (FPD), and flame thermionic detector (FTD). Among these detectors, the FID is most widely used, particularly for the purpose of detecting organic substances. The FID is a device that ionizes sample components in a sample gas by hydrogen flame and detects the resultant ion current. It has a wide dynamic range (the sample-concentration range within which the detection sensitivity shows a high degree of linearity) which has reached approximately six to seven orders of magnitude. However, the FID has drawbacks: firstly, its ionization efficiency is low, and therefore, its minimum detectable amount is not low enough; secondly, its ionization efficiencies for alcohols, aromatic substances, and chlorine-based substances are low; and thirdly, it requires hydrogen, which is a highly hazardous substance, and therefore, an explosion-proof apparatus or similar kind of special equipment must be provided, which makes the entire system difficult to operate.

In recent years, a dielectric barrier discharge ionization detector (which is hereinafter abbreviated as "BID") which employs ionization by dielectric barrier discharge plasma has been put to practical use as a new type of detector for a gas chromatograph (for example, see Patent Literatures 1 and 2, as well as Non Patent Literature 1).

In the BID described in the aforementioned literatures, a low-frequency AC high voltage is applied to the discharge electrodes circumferentially provided on a dielectric quartz glass tube, whereby a predetermined gas supplied into the tube line is ionized and non-equilibrium atmospheric pressure plasma is formed. The sample components in the sample gas injected into the tube line are ionized by the effects of the light emitted from this plasma, the excited species and the like. The thereby produced ions are collected by the collector electrode, and a detection signal corresponding to the amount of ions, and hence the amount of sample components, is generated. Generally, it is said that the mechanism of the ionization of sample components in the discharge ionization detector is the photoionization by high-energy vacuum ultraviolet light radiated from the plasma and the Penning ionization by meta-stable helium atoms produced by the plasma. As for the BID, as described in Non Patent Literature 1, it has been experimentally confirmed that the photoionization by the vacuum ultraviolet light mainly contributes to the ionization of the sample components.

CITATION LIST

Patent Literature

Patent Literature 1: JP 2010-60354 A
Patent Literature 2: WO 2012/169419

Non Patent Literature

Non Patent Literature 1: Shinada et al., "Yuudentai Baria Houden Wo Ouyou-shita Gasu Kuromatogurafu-you Shinki Ionka Kenshutsuki No Kaihatsu (Development of New Ionization Detector for Gas Chromatograph by Applying Dielectric Barrier Discharge)", *Shimadzu Hyouron (Shimadzu Review)*, Vol. 69, Nos. 3/4, Mar. 29, 2013

SUMMARY OF INVENTION

Technical Problem

In the aforementioned BID, the plasma is generated in a stable form, and furthermore, the quartz glass tube and other elements forming the gas passage will not be heated since the temperature of the plasma is low. Therefore, it is possible to reduce various noises due to a temporal fluctuation in the plasma, the heating of the tube line and other factors. As a result, a higher level of S/N ratio can be achieved than in the FID. The BID is also characterized by being capable of detecting a wide variety of organic and inorganic compounds with high sensitivity, which enables high-sensitivity quantitative determination of aldehydes, alcohols, halogens and other compounds for which it is difficult to obtain sufficient sensitivity with the FID.

That is to say, the BID has higher levels of detection sensitivity to low-concentration samples than the FID. However, as compared to the FID, the BID shows a greater decrease in the detection sensitivity to high-concentration samples. Therefore, as disclosed in Non Patent Literature 1, its detection dynamic range is no higher than approximately five orders of magnitude and is not comparable to the FID whose dynamic range is six to seven orders of magnitude. Due to such a narrowness of the dynamic range, a significant error may result if the BID is used in a quantitative analysis of a mixture of samples containing a plurality of sample components having significantly different concentrations or in a quantitative determination using the area percentage method (a quantitative determination method in which a sample concentration is calculated based on the ratio of each peak area to the total peak area on a chromatogram).

The present invention has been developed in view of such a problem, and its objective is to provide a BID capable of improving the dynamic range of detection to a level higher than that of the conventional BID by reducing the decrease in the detection sensitivity to high-concentration samples. The present invention also provides a method for tuning the BID.

Solution to Problem

As noted earlier, in the BID, the detection signal is produced by the ions which are generated from the sample components due mainly to the effect of the photoionization by the light emitted from the plasma and reach the collector electrode. Taking into account such a mechanism of detecting sample components in the BID, the present inventors have paid attention to the positional relationship between the collector electrode and the ejection port provided at the end of a sample injection tube for injecting sample gas into the gas passage, and have experimentally studied the relationship between the aforementioned positional relationship and the detection sensitivity in detail. As a result, it has been revealed that, in a BID having a structure disclosed in Non Patent Literature 1 or other references, if the positional relationship between the ejection port of the sample injection tube and the collector electrode is determined so as to optimize the detection sensitivity to low-concentration samples, the detection sensitivity to high-concentration samples will significantly decrease. It has also been revealed that changing the position of the ejection port of the sample injection tube relative to the collector electrode from the position which gives an optimum sensitivity toward the gas downstream side reduces the decrease in the detection sensitivity to high-concentration samples, although the detection sensitivity further decreases.

Such a phenomenon can be satisfactorily explained by inferring that, when the sample concentration is too high, the sample gas ejected from the sample injection tube into the gas passage considerably absorbs light and noticeably decreases the intensity of the light reaching the space near the collector electrode, causing a decrease in the ion generation efficiency in the space near the collector electrode. The present invention has been developed from the aforementioned experimental finding as well as from supplementary knowledge obtained by simulation calculations.

The dielectric barrier discharge ionization detector (BID) according to the present invention aimed at solving the previously described problem includes:

a discharge electrode;

a voltage supplier for applying AC voltage to the discharge electrode so as to generate plasma by causing a dielectric barrier discharge in a gas passage through which a predetermined gas is passed;

a sample gas injector placed on the gas downstream side from a generation area of the plasma within the gas passage, for ejecting a sample gas in a direction opposite to the flowing direction of the gas; and an ion detector placed on the gas downstream side from the generation area of the plasma within the gas passage, including a collector electrode for collecting ions generated from a sample component in the sample gas by light emitted from the plasma, wherein an ejection port for ejecting the sample gas into the gas passage in the sample gas injector is placed on the gas downstream side of the predetermined gas from the collector electrode.

The predetermined gas is not limited to a specific kind of gas. For example, it may be any gas selected from the group of helium, argon, nitrogen, neon and xenon, or a mixture of two or more of those kinds of gas.

In the BID according to the present invention, the light emitted from the plasma generation area reaches the vicinity of the collector electrode. Due to the effect of this light, sample components in the sample gas are ionized, and the resultant ions reach the collector electrode and are thereby detected. Therefore, the gas passage from the plasma generation area to the collector electrode is formed straight, and the predetermined gas passes by the collector electrode after flowing through the plasma generation area. It is also possible to adopt a passage configuration in which a portion of the predetermined gas after flowing through the plasma generation area is separated and discharged to the outside of the gas passage while the remaining portion is made to pass by the collector electrode. In any case, the sample gas ejected from the ejection port of the sample gas injector into the gas passage is pushed back by the predetermined gas flowing in the opposite direction to the ejecting direction, to be mixed with and carried by this predetermined gas.

Since the sample gas flows in the gas passage in this way, the sample concentration rapidly decreases with an increase in the distance from the ejection port of the sample gas injector on the gas upstream side of the predetermined gas.

Usually, to achieve high detection sensitivity, the ejection port of the sample gas injector is placed on the gas upstream side of the predetermined gas from the collector electrode so that the sample concentration in the vicinity of the collector electrode will be as high as possible.

By contrast, in the BID according to the present invention, the ejection port of the sample gas injector is placed on the gas downstream side of the predetermined gas from the collector electrode. Therefore, in the vicinity of the collector electrode, the sample gas is considerably diluted with the predetermined gas, which is disadvantageous in terms of detection sensitivity as compared to the case where the ejection port of the sample gas injector is placed on the gas upstream side of the predetermined gas from the collector electrode. However, an advantage exists in that the light emitted from the plasma reaches the vicinity of the collector electrode without undergoing significant attenuation even if the sample concentration of the sample gas is high. This is partly because the sample concentration in the vicinity of the collector electrode is decreased and partly because the space between the plasma generation area and the collector electrode is free from the high-concentration sample. As a result, the decrease in the detection sensitivity to the high-concentration sample is reduced and the linearity of the detection sensitivity is ensured over a wide range of sample concentrations.

The collector electrode has a certain width in the flowing direction of the predetermined gas. However, if a DC electric field is formed in the gas passage to promote the movement of the ions, the portion of the collector electrode at which the intensity of the electric field concentrates can be regarded as the effective collector electrode. Accordingly, in the case where the ion detector includes a bias electrode placed on the gas upstream or downstream side of the predetermined gas from the collector electrode in order to form the aforementioned DC electric field, the position of the end of the collector electrode on the side where the bias electrode is located can be regarded as the position of the effective collector electrode.

For example, if the bias electrode is placed on the gas upstream side of the predetermined gas from the collector electrode, the end of the collector electrode closer to the bias electrode is the effective collector electrode, and the ejection port of the sample gas injector only needs to be provided on the gas downstream side from the effective collector electrode which has no width in the flowing direction of the predetermined gas.

Naturally, if the ejection port of the sample gas injector is widely separated from the collector electrode toward the gas downstream side, the sample concentration in the space near the collector electrode will excessively decrease and the detection sensitivity and the S/N ratio will be equal to or lower than those of the FID. Accordingly, in order to obtain the sensitivity linearity over a wider range of sample concentrations as compared to the conventional BID while achieving adequately high detection sensitivity at least as compared to commonly used FIDs, the ejection port of the sample gas injector should preferably be configured to be placed at a distance of 7 mm or less from the collector electrode on the gas downstream side in the gas passage.

The method for tuning a dielectric barrier discharge ionization detector (BID) according to the present invention aimed at solving the previously described problem is a method for tuning a dielectric barrier discharge ionization detector including:

a discharge electrode;

a voltage supplier for applying AC voltage to the discharge electrode so as to generate plasma by causing a dielectric barrier discharge in a gas passage through which a predetermined gas is passed;

a sample gas injector placed on the gas downstream side from a generation area of the plasma within the gas passage, having an ejection port for ejecting a sample gas in a direction opposite to the flowing direction of the gas; and an ion detector placed on the gas downstream side from the generation area of the plasma within the gas passage, including a collector electrode for collecting ions generated from a sample component in the sample gas by light emitted from the plasma, and the method including:

a maximum position searching step, in which the position of the ejection port at which a detection sensitivity is maximized is searched for while the position of the ejection port in the sample gas injector is changed in the flowing direction of the predetermined gas within a predetermined range including the position of the collector electrode; and an ejection port position setting step, in which the position of the ejection port of the sample gas injector is set at a position which is on the gas downstream side of the predetermined gas from the position of the ejection port located in the maximum position searching step and at which a detection sensitivity within a range from 90 to 10% of the maximum value of the detection sensitivity is obtained.

In the maximum position searching step, when the position of the ejection port at which the detection sensitivity is maximized is searched for while the position of the ejection port in the sample gas injector is changed in the flowing direction of the predetermined gas within a space near the position of the collector electrode, the position of the ejection port at which the maximum value of the detection sensitivity is obtained is usually found at a position slightly shifted from the collector electrode toward the gas upstream side. As noted earlier, if the ejection port is set at this position, a noticeable decrease in the sensitivity to high-concentration samples occurs, while high detection sensitivity is obtained for low-concentration samples. Accordingly, in the subsequent step of setting the position of the ejection port, the ejection port is continuously moved toward the gas downstream side from the position where the maximum value of the detection sensitivity is obtained, so as to locate an appropriate position at which the detection sensitivity falls within a range from 90 to 10% of its maximum value, and the ejection port of the sample gas injector is set at the located position.

According to an experiment by the present inventors, when the position of the ejection port is set at a position where the detection sensitivity is 90% of the maximum value, the sample-concentration range within which the sensitivity linearity is obtained will be approximately doubled as compared to the case where the position of the ejection port is set at the position where the detection sensitivity is maximized An additional shift of the ejection port from that position toward the gas downstream side further widens the sample-concentration range within which the sensitivity linearity is obtained, while the detection sensitivity further decreases. Even when the position of the ejection port is moved to a position where the detection sensitivity is 10% of its maximum value, it is possible to achieve a detection sensitivity and S/N ratio adequately higher than those of the FID. Thus, as compared to the conventional BID, the sample-concentration range within which the sensitivity linearity is obtained can be dramatically widened.

Advantageous Effects of the Invention

With the dielectric barrier discharge ionization detector and its tuning method according to the present invention, the detection dynamic range can be widened as compared to conventional BIDs by a simple configuration or a simple tuning process while making use of the advantage that its detection sensitivity and S/N ratio are higher than those of FIDs. Specifically, the dynamic range can be widened to approximately six orders of magnitude, which is approximately ten times that of conventional BIDs and close to the level of FIDs. As a result, a high level of accuracy can be achieved even in a quantitative analysis of a mixture of samples having different concentrations or in a quantitative determination by the area percentage method.

BRIEF DESCRIPTION OF DRAWINGS

FIG. 3 is a graph showing the result of a measurement of the relationship between the position of the sample-gas ejection port relative to the position of the collector electrode and the detection sensitivity.

FIG. 4 is a graph showing the result of a measurement of the relationship between the sample concentration and the detection sensitivity for various values of the sample-gas injecting position (relative to the position at which the detection sensitivity is maximized).

DESCRIPTION OF EMBODIMENTS

Figure 1A:
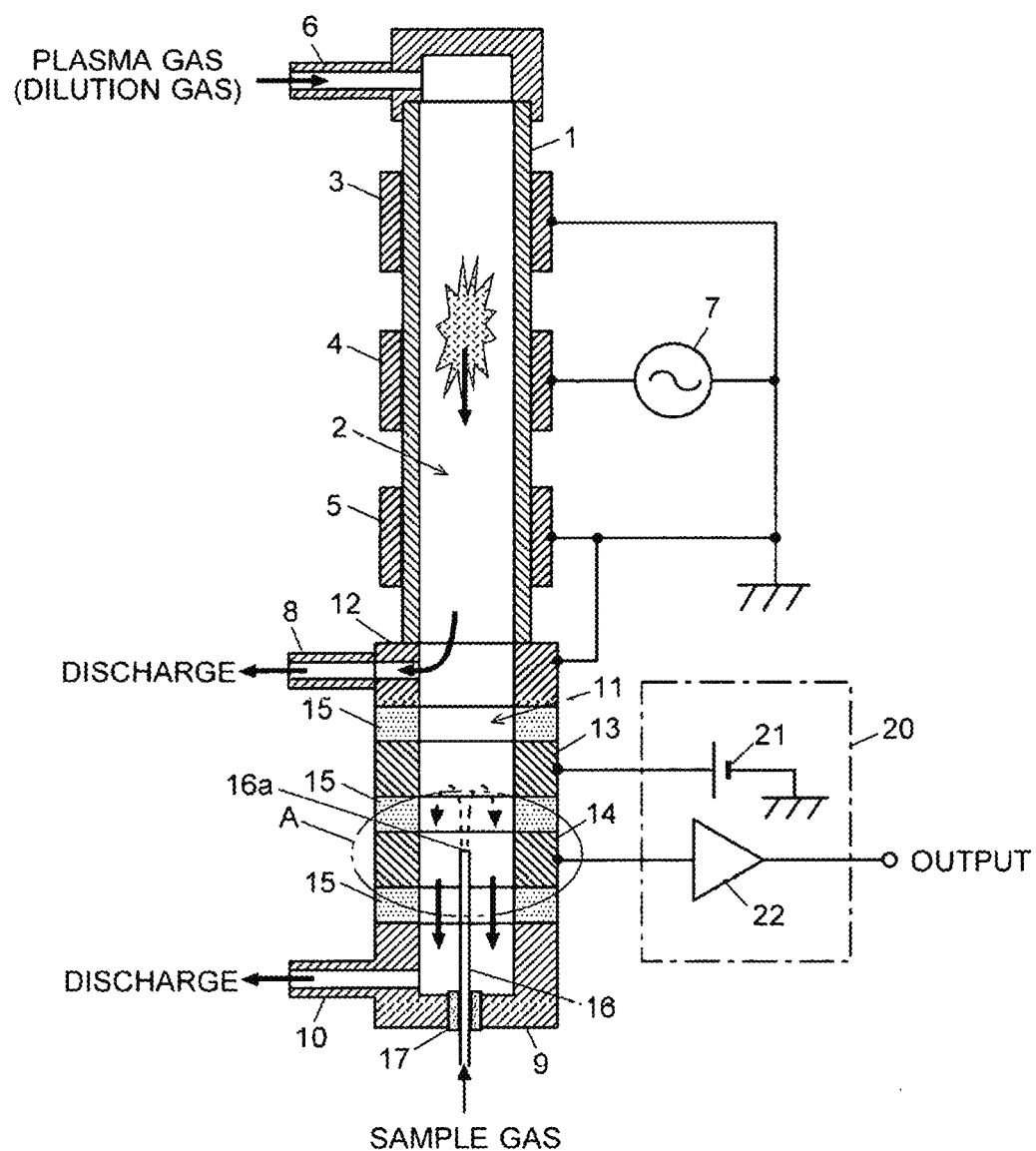
FIG. 1A is a schematic configuration diagram of a BID according to one embodiment of the present invention.
Figure 1B:
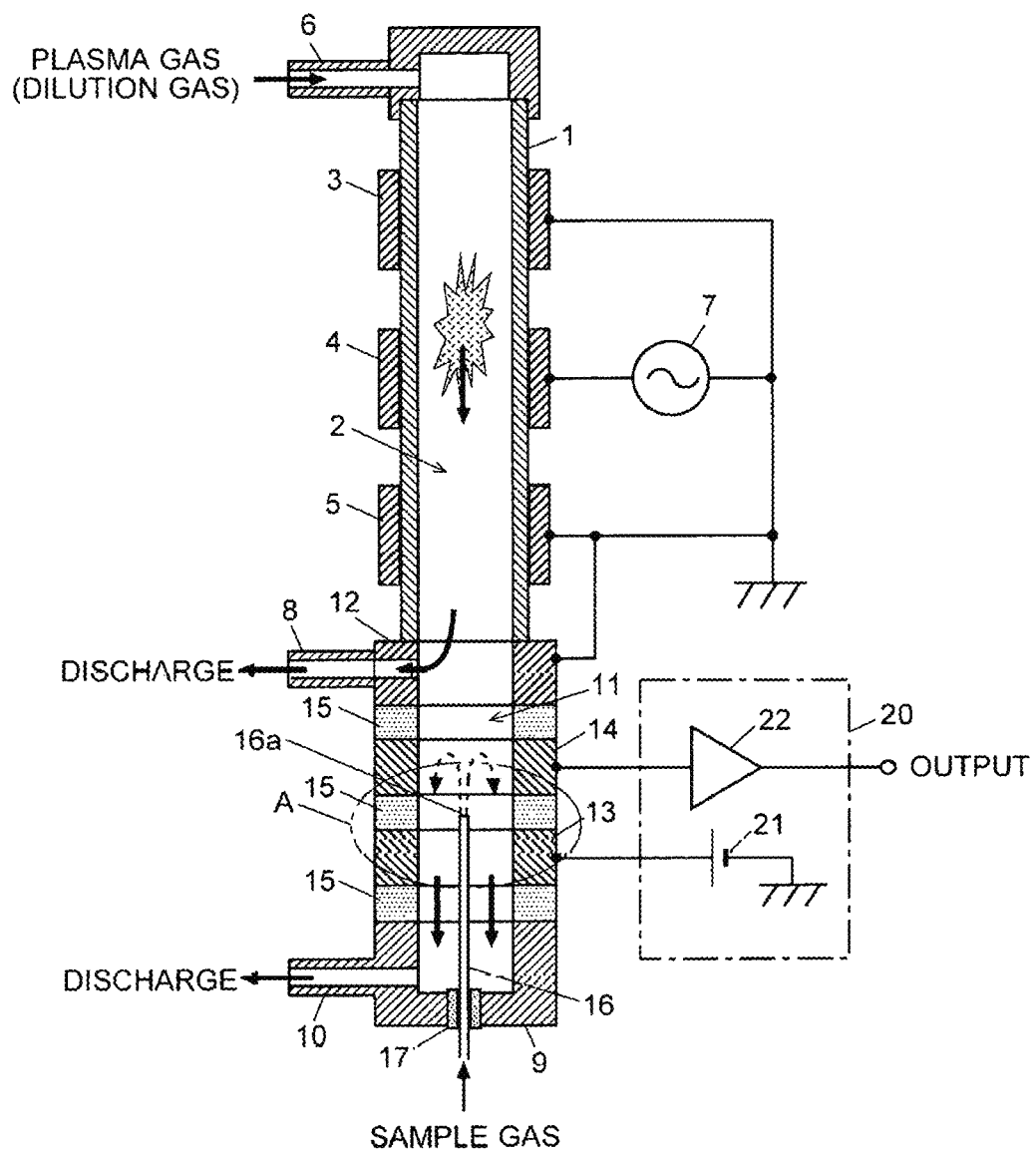
FIG. 1B is a schematic configuration diagram of a BID according to one embodiment of the present invention.

A BID and its tuning method according to one embodiment of the present invention is hereinafter described with reference to the attached drawings. FIG. 1 is a schematic configuration diagram of the BID of the present embodiment.

The BID of the present embodiment has a dielectric cylindrical tube 1 whose inner space serves as a first gas passage 2. On the outer wall surface of the dielectric cylindrical tube 1, ring-shaped plasma generation electrodes 3-5 made of an electrically conductive material (e.g. stainless steel or copper) are circumferentially provided at preset intervals in the flowing direction of the gas. A gas supply tube 6 is connected to the upper end of the dielectric cylindrical tube 1. Plasma gas doubling as dilution gas is supplied through this gas supply tube 6 into the first gas passage 2. Since the wall of the dielectric cylindrical tube 1 is present between the first gas passage 2 and each of the plasma generation electrodes 3-5, the wall itself functions as a dielectric coating layer which covers the surface of the plasma generation electrodes 3-5 and enables a dielectric barrier discharge (which will be described later) to occur.

Among the three plasma generation electrodes 3-5, the central plasma generation electrode 4 is connected to an excitation high-voltage AC power source 7, while the other two plasma generation electrodes 3 and 5 located on both sides of the central electrode 4 are grounded. Such a structure in which the plasma generation electrode 4, to which the high voltage is applied, is sandwiched between the grounded plasma generation electrodes 3 and 5 prevents the plasma produced by the electric discharge from spreading toward the upstream and downstream sides of the gas, thus limiting the substantial plasma generation area to the space between the two plasma generation electrodes 3 and 5. The excitation high-voltage AC power source 7 generates a high AC voltage of approximately 5-10 kV with a frequency of approximately 5-30 kHz (low frequency).

At the lower end of the dielectric cylindrical tube 1, a recoil electrode 12, a bias electrode 13 and a collector electrode 14, all of which have cylindrical shapes with the same inner diameter, are arranged along the flowing direction of the gas, with insulators 15 made of alumina, PTFE resin or a similar material inserted in between. A second gas passage 11 connected to the first gas passage 2 is formed inside those elements. A bypass discharge tube 8 for discharging a portion of the plasma gas to the outside is connected to the joining section of the first and second gas passages 2 and 11. A sample discharge tube 10 is connected to the end of the second gas passage 11.

The recoil electrode 12, which is grounded, prevents the charged particles in the plasma being carried by the gas flow from reaching the collector electrode 14, whereby noises are reduced and the S/N ratio of the detection signal is improved. The bias electrode 13 is connected to a bias DC power source 21, which is included in an ion-current detector unit 20. The collector electrode 14 is connected to a current amplifier 22, which is also included in the ion-current detector unit 20. In the second gas passage 11, the spaces inside the bias electrode 13, the collector electrode 14 and the intervening section correspond to the substantial ion detection area. A sample injection tube 16 having a small diameter is inserted via a seal part 17 into a tube-line end part 9 to which the sample discharge tube 10 is connected. A sample gas is supplied through this sample injection tube 16 into the second gas passage 11.

The operation of detecting a sample component contained in a sample gas in the present BID is hereinafter schematically described.

As shown by the arrows in FIG. 1, plasma gas is supplied through the gas supply tube 6 into the first gas passage 2 at a preset flow rate. The plasma gas is a kind of gas that is easily ionized. A typical example is helium. Argon, nitrogen, neon, xenon or a mixture of two or more of those kinds of gas may also be used. The plasma gas flows through the first gas passage 2 downward. A portion of this gas is discharged through the bypass discharge tube 8 to the outside, while the other portion serving as dilution gas flows through the second gas passage 11 downward, to be eventually discharged through the sample discharge tube 10 to the outside. Meanwhile, a sample gas containing a sample component is supplied through the sample injection tube 16 and ejected from the sample-gas ejection port 16*a* at its tip into the second gas passage 11. The ejection of the sample gas from the sample-gas ejection port 16*a* is made in the opposite direction to the flowing direction of the dilution gas. However, as shown by the arrows in FIG. 1, the sample gas is immediately pushed back, to be mixed with the dilution gas and carried downward.

While the plasma gas is flowing through the first gas passage 2 in the previously described way, the excitation high-voltage AC power source 7 applies high AC voltage to the plasma generation electrode 4. As a result, a dielectric barrier discharge occurs in the plasma generation area located between the plasma generation electrodes 3 and 5 in the first gas passage 2, whereby the plasma gas is ionized over a wide range and a cloud of plasma (atmospheric pressure non-equilibrium micro plasma) is generated. The excitation light emitted from the atmospheric pressure non-equilibrium micro plasma passes through the first and second gas passages 2 and 11, reaches the site where the sample gas is present, and ionizes the sample component in the sample gas. Due to the effect of the electric field formed by the DC voltage applied to the bias electrode 13, the generated ions move toward the collector electrode 14, where the ions give or receive electrons to or from the collector electrode 14. As a result, an ion current which corresponds to the amount of ions generated from the sample component, and hence to the amount of sample component, is fed to the current amplifier 22, which amplifies the ion current and outputs a detection signal. In this manner, the present BID produces a detection signal corresponding to the amount (concentration) of sample component contained in the sample gas introduced through the sample injection tube 16.

The basic components of the BID of the present embodiment are the same as those of commonly used BIDs. The previously described detecting operation is also basically the same as that of commonly used BIDs. The structural characteristic of the BID of the present embodiment is that the insertion length of the sample injection tube 16 in the second gas passage 11 is adjusted so that the position of the sample-gas ejection port 16*a* of the sample injection tube 16 relative to the collector electrode 14 satisfies unique conditions different from conventional BIDs.

Figure 2A:
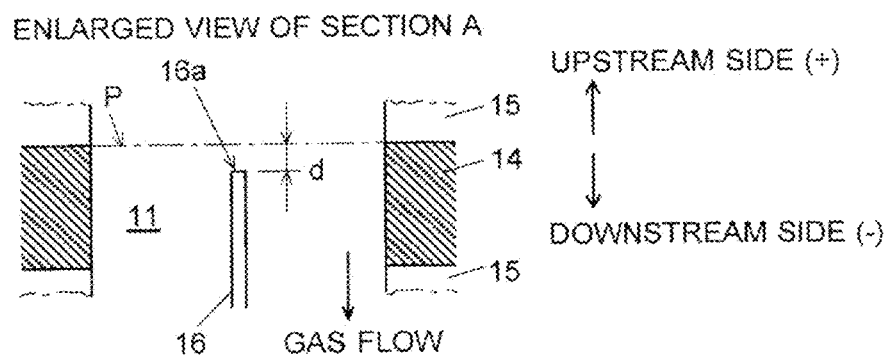
FIG. 2A is an enlarged view of section A in FIG. 1A.

FIG. 2A is an enlarged view of section A in FIG. 1. In the BID of the present embodiment, the sample injection tube 16 is inserted into the second gas passage 11 so that the sample-gas ejection port 16*a* of the sample injection tube 16 is shifted downward (i.e. toward the downstream side of the dilution gas) by a predetermined distance d from the end P of the collector electrode 14 on the side facing the bias electrode 13 (i.e. on the upper side in FIG. 2A). In conventionally and commonly used BIDs, the sample-gas ejection port 16*a* is located at a position shifted upward (i.e. toward the upstream side of the dilution gas) from the end P by a predetermined distance. In this respect, the BID of the present embodiment differs from conventional BIDs. Since the end P is the portion closest to the bias electrode 13 in the collector electrode 14, the DC electric field formed in the second gas passage 11 by applying the DC voltage to the bias electrode 13 concentrates at this end P. Accordingly, it is this end P that most significantly contributes to the collection of the ions in the collector electrode 14. Therefore, it is possible to regard the position of the end P as the position of the effective collector electrode 14.

The reason why the sample-gas ejection port 16*a* is placed on the downstream side of the dilution gas relative to the end P in the previously described manner is hereinafter described in comparison to the configuration in a conventional BID.

Figure 2B:
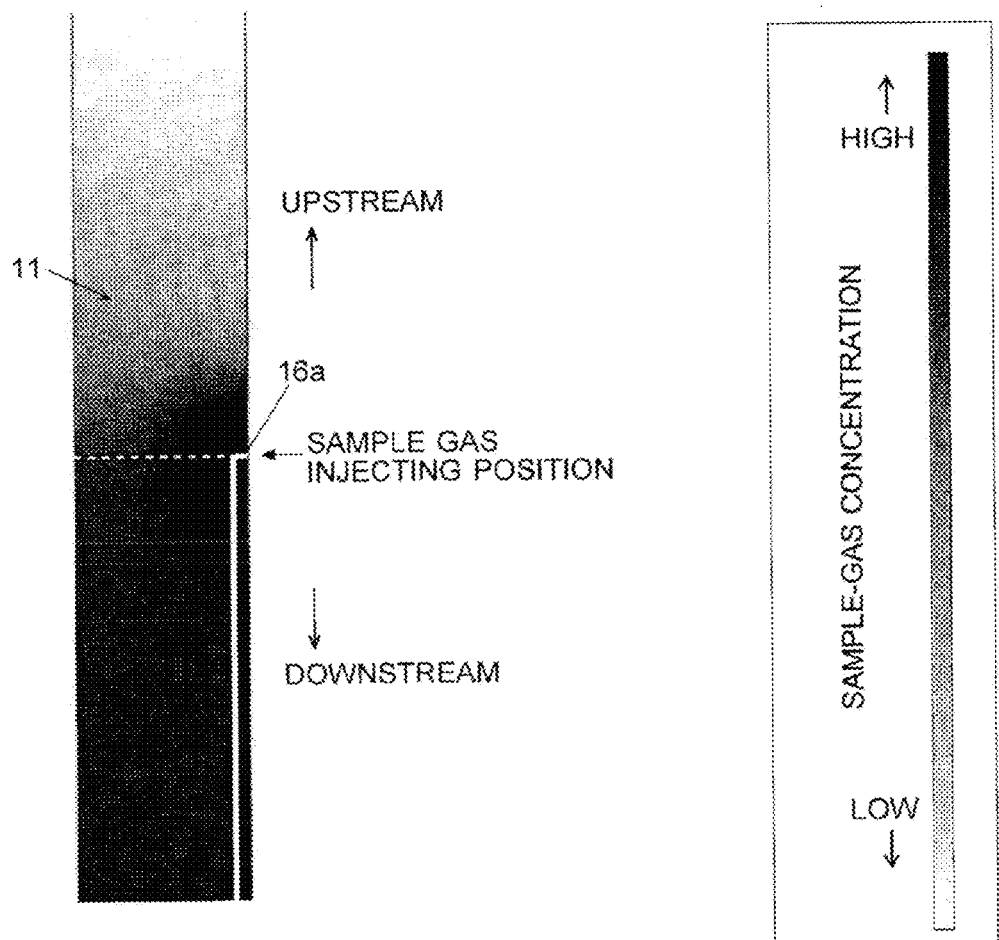
FIG. 2B shows the result of a simulation of the distribution of a sample gas concentration in a region around section A.
Figure 2C:
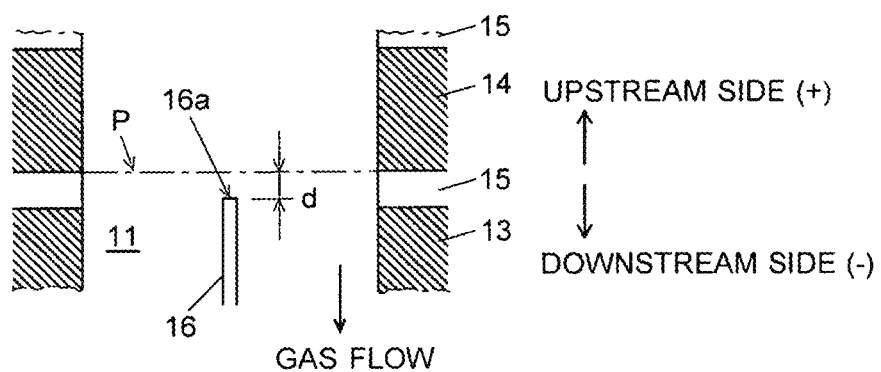
FIG. 2C is an enlarged view of section A in FIG. 1B.

FIG. 2B shows the result of a simulation calculation of the distribution of the sample-gas concentration in a region around section A. The configuration and measurement conditions assumed in the simulation are as follows: the inner diameter of the collector electrode 14 is 3 mm; the inner diameter of the sample injection tube 16 is 0.25 mm; the flow rate of the dilution gas is 10 mL/min; and the flow rate of the sample gas is 1 mL/min. The sample gas ejected upward from the sample-gas ejection port 16a of the sample injection tube 16 is pushed by the downward flow of the dilution gas (plasma gas) and changes its direction to flow downward. Normally, the diffusion rate of the sample gas is so high that the gas concentration in the radial direction of the second gas passage 11 quickly becomes uniform. As a result, the distribution of the sample-gas concentration around the sample-gas ejection port 16a will be such that the concentration changes with distance on each of the upstream and downstream sides of the dilution gas, as shown in FIG. 2B.

As noted earlier, the ionization mechanism in the BID is mainly the photoionization by vacuum ultraviolet light from the plasma. Accordingly, the ion generation efficiency normally improves with an increase in the light intensity. If the light intensity is the same, the amount of ions originating from the sample component increases with an increase in the amount of sample component present in the region illuminated with the light. However, the electrons released from the sample molecules (or atoms) in the photoionization stay in the vicinity of the ion, and therefore, they are comparatively easy to recombine. Therefore, an ion generated in a region distant from the collector electrode 14 easily disappears before reaching this electrode 14. Accordingly, it is probably the ions generated in the vicinity of the collector electrode 14 that is mainly reflected by the detection signal. From these facts, it is possible to suppose that the amount of ionic charges collected by the collector electrode 14 can be expressed by the following formula:

[Amount of Ionic Charges: C]∝[Sample Concentration in the Vicinity of Collector Electrode 14]× [Light Intensity of Vacuum Ultraviolet Light Reaching the Vicinity of Collector Electrode 14]   (1)

The simulation result shown in FIG. 2B demonstrates the following two facts concerning the relationship between the position of the sample-gas ejection port 16a relative to the position of the collector electrode 14 and the detection sensitivity:

[1] Changing the position of the sample-gas ejection port 16a toward the downstream side of the dilution gas relative to the position of the collector electrode 14 decreases the sample concentration in the vicinity of the collector electrode 14.

[2] Changing the position of the sample-gas ejection port 16a toward the upstream side of the dilution gas relative to the position of the collector electrode 14 increases the distance which the sample gas ejected into the second gas passage 11 and carried by the dilution gas needs to travel before reaching the vicinity of the collector electrode 14. The light emitted from the plasma needs to pass through this sample gas before reaching the region near the collector electrode 14. Therefore, changing the position of the sample-gas ejection port 16a toward the upstream side of the dilution gas relative to the position of the collector electrode 14 increases the optical path length in the sample-gas atmosphere, which causes a greater amount of light absorption by the sample gas and a consequent decrease in the intensity of light reaching the region near the collector electrode 14.

If the relationship between the position of the sample-gas ejection port 16a relative to the collector electrode 14 and the detection sensitivity is considered taking into account these two conclusions and the relationship represented by formula (1), it is easy to deduce that the detection sensitivity is maximized at a certain relative position, and that shifting the sample-gas ejection port 16a from this position toward any of the upstream and downstream sides of the dilution gas decreases the detection sensitivity. To confirm this deduction, an experiment was conducted, in which nitrogen was used as the sample gas and the detection sensitivity was measured while the insertion length of the sample injection tube 16 was changed so as to vertically move the sample-gas ejection port 16a relative to the position of the collector electrode 14.

FIG. 3 is a graph showing the measured result of the relationship between the position of the sample-gas ejection port 16a relative to the position of the collector electrode 14 and the detection sensitivity. The horizontal axis indicates the relative position, where the value "0" means that the collector electrode 14 and the sample-gas ejection port 16a are at the same position. The value becomes positive when the sample-gas ejection port 16a is on the upstream side of the dilution gas relative to the zero position, and negative when the sample-gas ejection port 16a is on the downstream side of the dilution gas. That is to say, the absolute value of the numerical value on the horizontal axis corresponds to distance d in FIG. 2A. It should be noted that the position of the collector electrode 14 in the present context is the end position P shown in FIG. 2A.

The result shown in FIG. 3 confirms that the detection sensitivity is maximized at a certain relative position. In the present example, the detection sensitivity is maximized when the sample-gas ejection port 16a is located at d=1.5 mm relative to the collector electrode 14 on the upstream side of the dilution gas. As noted earlier, in conventionally and commonly used BIDs, the sample-gas ejection port 16a is configured to be located on the upstream side of the dilution gas relative to the collector electrode 14. The measured result shown in FIG. 3 demonstrates that such a configuration is appropriate from the viewpoint of improving the detection sensitivity to the highest possible level.

FIG. 4 is a graph showing a measured result of the relationship between the sample concentration and the sensitivity ratio at a plurality of sample-gas injecting positions. The sample-gas injecting position which gives the maximum value of detection sensitivity in FIG. 3 (i.e. the relative position of +1.5 mm in FIG. 3; this position is hereinafter called the "sensitivity-maximized position") is defined as 0 mm, with the positive values representing the upstream side of the dilution gas relative to the sensitivity-maximized position and the negative values representing the downstream side of the dilution gas. The sensitivity ratio indicated by the vertical axis is a relative value, with the value "1" representing the maximum value of detection sensitivity. The measured result demonstrates the following facts:

[1] When the sample-gas ejection port 16a is on the upstream side of the dilution gas relative to the sensitivity-maximized position (the sample-gas injecting positions of +3 mm and +5 mm in FIG. 4), the sensitivity significantly decreases within a sample-concentration range of 0.1% or higher.

[2] When the sample-gas ejection port 16a is on the downstream side of the dilution gas relative to the sensitivity-maximized position (the sample-gas injecting positions of −2 mm and −4 mm in FIG. 4), the sample-concentration range within which the detection sensitivity shows a high degree of linearity expands toward the higher-concentration side as the distance from the sensitivity-maximized position increases.

The previously described results demonstrate that it is possible to reduce the decrease in the sensitivity to high-concentration samples and widen the sample-concentration range having a high degree of sensitivity linearity (i.e. the dynamic range) by locating, as a reference position, a sample-gas injecting position at which the detection sensitivity is maximized (i.e. the sensitivity-maximized position) and then placing the sample-gas ejection port 16a on the downstream side of the dilution gas relative to the reference position.

The sensitivity-maximized position in the previous embodiment is located at a relative position of +1.5 mm in FIG. 3. Naturally, this position changes depending on the structure of the detector (e.g. the inner diameter of the tube line) and the measurement conditions (e.g. the flow rate of the dilution gas). However, even if the structure of the detector and/or the measurement conditions are changed, the relative distribution of the sample-gas concentration substantially remain unchanged in its shape from that shown in FIG. 2B except the horizontal and vertical extents, and the overall tendency of the distribution will not significantly change. Therefore, by taking the following procedure regardless of the structure of the detector and the measurement conditions, it is possible to assuredly improve the dynamic range as compared to the case where the sample-gas ejection port 16a is placed at the sensitivity-maximized position:

[Step S1] While the position of the sample-gas ejection port 16a is changed relative to the collector electrode 14 in the flowing direction of the dilution gas, the detection sensitivity for a predetermined sample (e.g. a standard sample) is measured to search for the position at which the detection sensitivity is maximized. In other words, the sensitivity-maximized position is determined.

[Step S2] The position of the sample-gas ejection port 16a is shifted from the sensitivity-maximized position toward the downstream side of the dilution gas by an appropriate distance.

The sample-concentration range in which the detection sensitivity has a linearity, i.e. the range of sensitivity linearity, varies depending on the amount of shift in Step S2.

Figure 5:
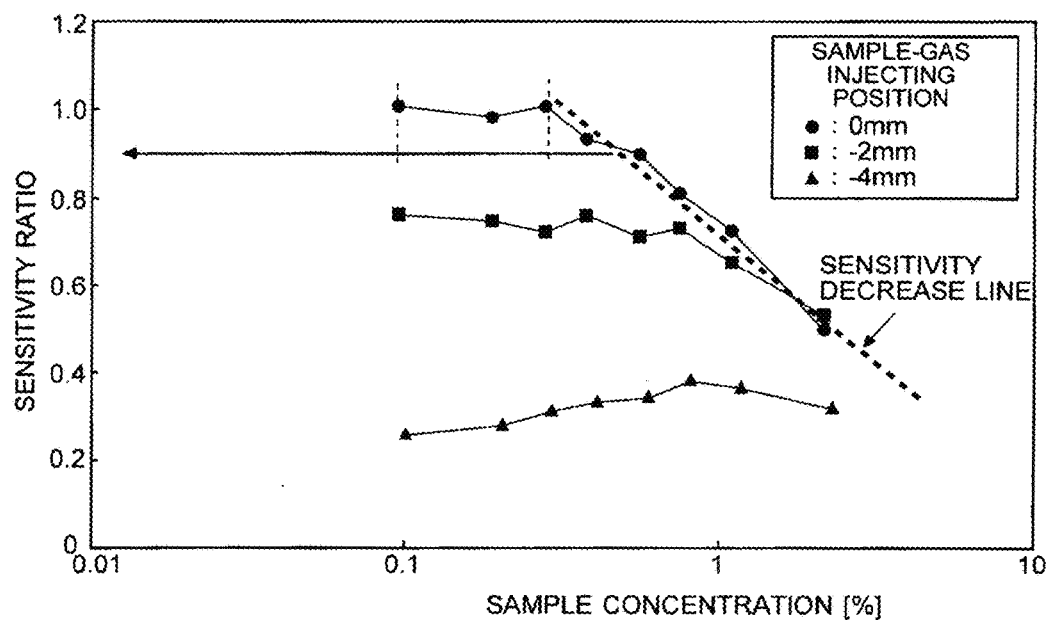
FIG. 5 is a diagram illustrating the sensitivity linearity based on the relationship between the sample concentration and the detection sensitivity for various values of the sample-gas injecting position (relative to the position at which the detection sensitivity is maximized).

FIG. 5 is a graph showing the data with the sample-gas injecting position being zero or negative in FIG. 4. In FIG. 5, the data obtained at a sample-gas injecting position of −2 mm show a decrease in sensitivity along the sensitivity decrease line (shown by the broken line) of the data obtained at a sample-gas injecting position of 0 mm. In this case, although the sensitivity ratio is decreased to approximately 75% of the maximum sensitivity value as a result of the shift of the sample-gas ejection port 16a from the sensitivity-maximized position, the range of sensitivity linearity is approximately tripled, from approximately 0.3% to roughly 1%. This result suggests that changing the position of the sample-gas ejection port 16a toward the downstream side of the dilution gas relative to the position of the collector electrode 14 produces an adequate effect of widening the range of sensitivity linearity, although the level of sensitivity decreases.

This effect should preferably be large enough to make the range of sensitivity linearity equal to or wider than two times the range observed at the sensitivity-maximized position. The aforementioned sensitivity decrease line in FIG. 5 shows that the range of sensitivity linearity can be doubled or even made wider by moving the sample-gas ejection port 16a to a position where the sensitivity ratio is equal to or lower than 90% of the value corresponding to the maximum detection sensitivity. Accordingly, in Step S2, it is preferable to adaptively shift the sample-gas ejection port 16a from the sensitivity-maximized position toward the downstream side of the dilution gas so that the detection sensitivity becomes equal to or lower than 90% of its maximum value, rather than previously specifying the amount of shift.

In the BID of the present embodiment, it is possible to widen the range of sensitivity linearity while minimizing the decrease in the detection sensitivity from its maximum value, by adjusting the insertion length of the sample injection tube 16 into the second gas passage 11 by the previously described tuning procedure. However, the effect of widening the range of sensitivity linearity while minimizing the decrease in the detection sensitivity from its maximum value can also be obtained, without the tuning task, by previously setting the position of the sample-gas ejection port 16a of the sample injection tube 16 relative to the position of the collector electrode 14. That is to say, FIG. 3 demonstrates that the detection sensitivity is always equal to or lower than 90% of its maximum value when the sample-gas ejection port 16a is located on the downstream side of the dilution gas relative to the position of the collector electrode 14 in the previously described manner. Accordingly, the desired effect can be obtained by merely placing the sample-gas ejection port 16a on the downstream side of the dilution gas relative to the position of the collector electrode 14.

Discussed hereinafter is an appropriate range of the placement position of the sample-gas ejection port 16a relative to the position of the collector electrode 14. When the position of the sample-gas ejection port 16a is changed toward the downstream side of the dilution gas in the previously described manner, the detection sensitivity decreases in exchange for the widening of the dynamic range. Therefore, the allowable range of the shift of the sample-gas ejection port 16a depends on the lower limit of the permissible detection sensitivity. The detection sensitivity (ionization efficiency) of commonly used BIDs is approximately 50 times that of FIDs. Since the high detection sensitivity is the most important advantage of BIDs, it is minimally necessary to achieve a detection sensitivity adequately higher than that of FIDs. Taking this into account, it is desirable to prevent the detection sensitivity from being decreased to a level lower than approximately one tenth of its maximum value.

Figure 6:
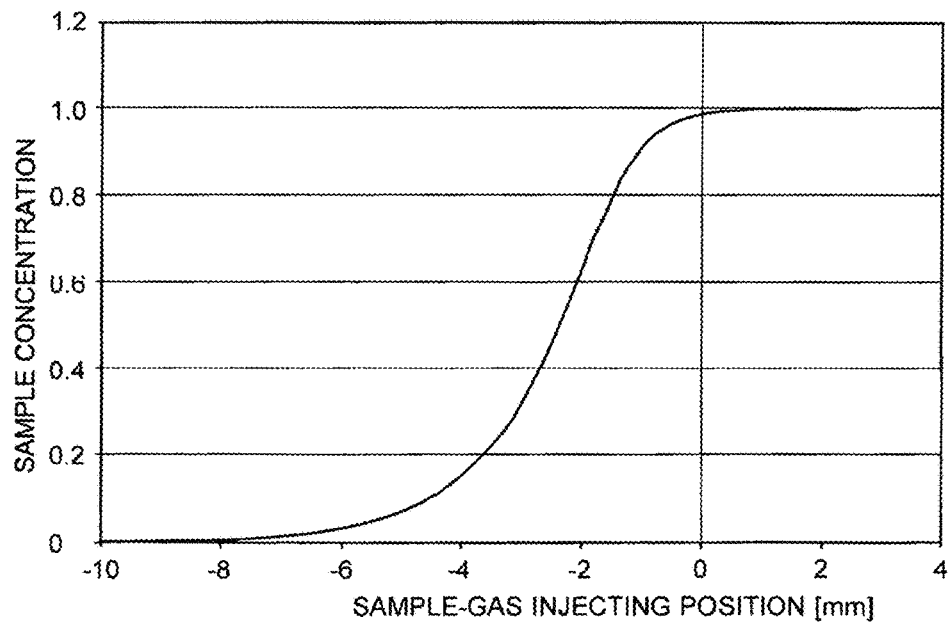
FIG. 6 is a graph showing the result of a simulation of the relationship between the sample-gas injecting position (relative to the position at which the detection sensitivity is maximized) and the sample-gas concentration at the position of the collector electrode.

As shown by formula (1), the detection sensitivity is proportional to the sample concentration in the vicinity of the collector electrode 14. When the sample-gas ejection port 16a is located on the downstream side of the dilution gas relative to the collector electrode 14, the sample concentration in the vicinity of the collector electrode 14 is determined by what amount of sample gas diffuses into the upstream area against the flow of the dilution gas and reaches the vicinity of the collector electrode 14. That is to say, it depends on the balance between the flow rate of the dilution gas coming from above and the diffusion rate of the sample gas. The diffusion rate of the sample gas depends on the gas species. However, this dependency is not so heavy and the diffusion rate can be regarded as almost uniform. Thus, the primary parameter which affects the range of the appropriate position of the sample-gas ejection port 16a is the flow rate of the dilution gas. In the case of the measurement shown in FIG. 4, the flow rate of the dilution gas through the second gas passage 11 is 12.5 mL/min, and the inner diameter of this tube line is 3 mm. Therefore, the flow rate of the dilution gas is approximately 30 mm/sec. Under this condition, a simulation has been performed to calculate how the sample concentration in the vicinity of the collector electrode 14 changes when the sample-gas ejection port 16a is moved in the flowing direction of the dilution gas. The result is shown in FIG. 6. The horizontal axis in FIG. 6 indicates the values of the sample-gas injection position used in FIGS. 4 and 5.

Table 1 shows the sensitivity ratios actually measured at sample-gas injecting positions of −2 mm and −4 mm (the result shown in FIG. 4) and the corresponding sample concentrations obtained by the simulation calculation (the result shown in FIG. 6).

TABLE 1

| Sample-Gas Injecting Position | Measured Sensitivity | Calculated Concentration |
| --- | --- | --- |
| −2 mm | ~0.8 | 0.6 |
| −4 mm | 0.2~0.3 | 0.15 |

Although the measured sensitivities are slightly larger, the two kinds of values show the same tendency of change with respect to the sample-gas injecting position. FIG. 6 demonstrates that, under the conditions of the measurement example, the detection sensitivity decreases to one tenth when the sample-gas injecting position is approximately −6 mm. Therefore, provided that the range of the sample-gas injecting position should be determined under a given flow rate of the dilution gas, the lower limit of the sample-gas injecting position is −6 mm when the flow rate of the dilution gas is 30 mm/sec. That is to say, by setting the sample-gas injecting position within a range from 0 to −6 mm, it is possible to make the dynamic range wider than that of conventional BIDs while adequately maintaining the superiority in the detection sensitivity over FIDs.

When the flow rate of the dilution gas is changed, the lower limit of the sample-gas injecting position becomes smaller as the flow rate increases. In the present case, the lower limit can be determined by $a \times x = 180$, where $a$ is the flow rate of the dilution gas in mm/sec and $\chi$ is the sample-gas injecting position in mm. This equation suggests that the absolute value of the lower limit of the sample-gas injecting position can be set at a larger value as the flow rate of the dilution gas is decreased. However, setting the dilution-gas flow rate at a level lower than 30 mm/sec is impracticable, since this setting may possibly cause an excessive diffusion of the sample gas from the sample-gas ejection port 16a into the upstream side of the dilution gas, allowing the gas to reach the section where the plasma generation electrodes 3-5 are located and contaminate the inner wall of the tube line. Empirically, the contamination becomes noticeable if the dilution-gas flow rate is decreased to approximately 15 mm/sec. Therefore, the practical lower limit of the dilution-gas flow rate is approximately 70-80% of 30 mm/sec. The lower limit of the sample-gas injecting position can also be accordingly increased by 20-30%, from −6 mm to approximately −7 mm or −8 mm.

Thus, it can be said that, when a practically allowable change in the flow rate of the dilution gas is taken into account, the lower limit of the sample-gas injecting position which allows the dynamic range to be wider than that of conventional BIDs while adequately maintaining the superiority in the detection sensitivity over FIDs is approximately −8 mm. This is equivalent to saying that the sample-gas ejection port 16a can be placed at a maximum distance of approximately −7 mm from the collector electrode 14 on the downstream side of the dilution gas. Thus, it is possible to conclude that the original goal can be accomplished by determining the insertion length of the sample injection tube 16 so that the sample-gas ejection port 16a is located on the downstream side of the dilution gas within a maximum distance of approximately 7 mm from the position of the collector electrode 14.

In the BID of the previously described embodiment, a portion of the plasma gas (dilution gas) is discharged from the joining section of the first and second gas passages 2 and 11 through the bypass discharge tube 8. It is also possible to adopt a configuration without the bypass discharge tube 8. In that case, the entire amount of plasma gas supplied through the gas supply tube 6 passes through the second gas passage 11 and is discharged from the sample discharge tube 10. Naturally, this configuration also allows the present invention to be applied as is.

In the BID of the previously described embodiment, the bias electrode 13 is located on the upstream side of the dilution gas relative to the collector electrode 14. It is also possible to consider a configuration having the bias electrode 13 located on the downstream side of the dilution gas relative to the collector electrode 14. In that case, it is at the lower edge of the collector electrode 14 that the electric field formed in the second gas passage 11 by the DC bias voltage applied to the bias electrode 13 concentrates, i.e. the lower edge of the collector electrode 14 is the position of the effective collector electrode 14. Accordingly, the collector electrode 14 should be made thin or the sample-gas ejection port 16a should be lowered so that the sample-gas ejection port 16a is positioned downstream to the lower edge of the collector electrode 14 in the flowing direction of the dilution gas.

It should be noted that the previously described embodiment is a mere example of the present invention, and any change, modification or addition appropriately made within the spirit of the present invention in any respect other than those already described will naturally fall within the scope of claims of the present patent application.

REFERENCE SIGNS LIST

1 . . . Dielectric Cylindrical Tube
2 . . . First Gas Passage
3, 4, 5 . . . Plasma Generation Electrode
6 . . . Gas Supply Tube
7 . . . Excitation High-Voltage AC Power Source
8 . . . Bypass Discharge Tube
9 . . . Tube-Line End Part
10 . . . Sample Discharge Tube
11 . . . Second Gas Passage
12 . . . Recoil Electrode
13 . . . Bias Electrode
14 . . . Collector Electrode
15 . . . Insulator
16 . . . Sample Injection Tube
16a . . . Sample-Gas Ejection Port
17 . . . Seal Part
20 . . . Ion-Current Detector Unit
21 . . . Bias DC Power Source
22 . . . Current Amplifier

The invention claimed is:

1. A dielectric barrier discharge ionization detector, comprising:
   a discharge electrode;
   a voltage supplier for applying AC voltage to the discharge electrode so as to generate plasma by causing a dielectric barrier discharge in a gas passage through which a predetermined gas is passed;

a sample gas injector placed on a gas downstream side from a generation area of the plasma within the gas passage, for ejecting a sample gas in a direction opposite to a flowing direction of the gas; and an ion detector placed on the gas downstream side from the generation area of the plasma within the gas passage, including a collector electrode for collecting ions generated from a sample component in the sample gas by light emitted from the plasma, wherein an ejection port for ejecting the sample gas into the gas passage in the sample gas injector is placed on the gas downstream side of the predetermined gas from the collector electrode;

the ion detector includes a bias electrode placed on the gas upstream side of the predetermined gas from the collector electrode in order to form a DC electric field for promoting a movement of ions in the gas passage, and the ejection port of the sample-gas injector is placed on a gas downstream side from an end of the collector electrode on a side where the bias electrode is located.

2. The dielectric barrier discharge ionization detector according to claim 1, wherein the ejection port of the sample-gas injector is placed at a distance of 7 mm or less from the collector electrode on the gas downstream side in the gas passage.

3. A dielectric barrier discharge ionization detector, comprising:

a discharge electrode;

a voltage supplier for applying AC voltage to the discharge electrode so as to generate plasma by causing a dielectric barrier discharge in a gas passage through which a predetermined gas is passed;

a sample gas injector placed on a gas downstream side from a generation area of the plasma within the gas passage, for ejecting a sample gas in a direction opposite to a flowing direction of the gas; and an ion detector placed on the gas downstream side from the generation area of the plasma within the gas passage, including a collector electrode for collecting ions generated from a sample component in the sample gas by light emitted from the plasma, wherein an ejection port for ejecting the sample gas into the gas passage in the sample gas injector is placed on the gas downstream side of the predetermined gas from the collector electrode, the ion detector includes a bias electrode placed on the gas downstream side of the predetermined gas from the collector electrode in order to form a DC electric field for promoting a movement of ions in the gas passage; and the ejection port of the sample-gas injector is placed on a gas downstream side from an end of the collector electrode on a side where the bias electrode is located and is placed on a gas upstream side from an end of a gas downstream side of the bias electrode.

4. The dielectric barrier discharge ionization detector according to claim 3, wherein the ejection port of the sample-gas injector is placed at a distance of 7 mm or less from the collector electrode on the gas downstream side in the gas passage.

5. A dielectric barrier discharge ionization detector, comprising:

a discharge electrode;

a voltage supplier for applying AC voltage to the discharge electrode so as to generate plasma by causing a dielectric barrier discharge in a gas passage through which a predetermined gas is passed;

a sample gas injector placed on a gas downstream side from a generation area of the plasma within the gas passage, for ejecting a sample gas in a direction opposite to a flowing direction of the gas; and an ion detector placed on the gas downstream side from the generation area of the plasma within the gas passage, including a collector electrode for collecting ions generated from a sample component in the sample gas by light emitted from the plasma, wherein an ejection port for ejecting the sample gas into the gas passage in the sample gas injector is placed on the gas downstream side of the predetermined gas from the collector electrode, and the ejection port of the sample gas injector is placed at a position on the gas downstream side of the predetermined gas from a position at which a detection sensitivity is maximized, the latter position determined by changing the position of the ejection port of the sample-gas injector in the flowing direction of the predetermined gas, and the former position being a position at which the detection sensitivity is within a range from 90 to 10% of a maximum value of the detection sensitivity.

6. A dielectric barrier discharge ionization detector, comprising:

a discharge electrode;

a voltage supplier for applying AC voltage to the discharge electrode so as to generate plasma by causing a dielectric barrier discharge in a gas passage through which a predetermined gas is passed;

a sample gas injector placed on a gas downstream side from a generation area of the plasma within the gas passage, for ejecting a sample gas in a direction opposite to a flowing direction of the gas; and an ion detector placed on the gas downstream side from the generation area of the plasma within the gas passage, including a collector electrode for collecting ions generated from a sample component in the sample gas by light emitted from the plasma, wherein an ejection port for ejecting the sample gas into the gas passage in the sample gas injector is placed on the gas downstream side of the predetermined gas from the collector electrode, the ion detector includes a bias electrode placed on the gas upstream or downstream side of the predetermined gas from the collector electrode in order to form a DC electric field for promoting a movement of ions in the gas passage, the ejection port of the sample-gas injector is placed on a gas downstream side from an end of the collector electrode on a side where the bias electrode is located, and the ejection port of the sample gas injector is placed at a position on the gas downstream side of the predetermined gas from a position at which a detection sensitivity is maximized, the latter position determined by changing the position of the ejection port of the sample-gas injector in the flowing direction of the predetermined gas, and the former position being a position at which the detection sensitivity is within a range from 90 to 10% of a maximum value of the detection sensitivity.

7. A dielectric barrier discharge ionization detector, comprising:

a discharge electrode;

a voltage supplier for applying AC voltage to the discharge electrode so as to generate plasma by causing a dielectric barrier discharge in a gas passage through which a predetermined gas is passed;

a sample gas injector placed on a gas downstream side from a generation area of the plasma within the gas passage, for ejecting a sample gas in a direction opposite to a flowing direction of the gas; and an ion detector placed on the gas downstream side from the generation area of the plasma within the gas passage, including a collector electrode for collecting ions generated from a sample component in the sample gas by light emitted from the plasma, wherein an ejection port for ejecting the sample gas into the gas passage in the sample gas injector is placed on the gas downstream side of the predetermined gas from the collector electrode, the ejection port of the sample-gas injector is placed at a distance of 7 mm or less from the collector electrode on the gas downstream side in the gas passage, and the ejection port of the sample gas injector is placed at a position on the gas downstream side of the predetermined gas from a position at which a detection sensitivity is maximized, the latter position determined by changing the position of the ejection port of the sample-gas injector in the flowing direction of the predetermined gas, and the former position being a position at which the detection sensitivity is within a range from 90 to 10% of a maximum value of the detection sensitivity.

8. A dielectric barrier discharge ionization detector, comprising:

a discharge electrode;

a voltage supplier for applying AC voltage to the discharge electrode so as to generate plasma by causing a dielectric barrier discharge in a gas passage through which a predetermined gas is passed;

a sample gas injector placed on a gas downstream side from a generation area of the plasma within the gas passage, for ejecting a sample gas in a direction opposite to a flowing direction of the gas; and an ion detector placed on the gas downstream side from the generation area of the plasma within the gas passage, including a collector electrode for collecting ions generated from a sample component in the sample gas by light emitted from the plasma, wherein an ejection port for ejecting the sample gas into the gas passage in the sample gas injector is placed on the gas downstream side of the predetermined gas from the collector electrode, the ion detector includes a bias electrode placed on the gas upstream or downstream side of the predetermined gas from the collector electrode in order to form a DC electric field for promoting a movement of ions in the gas passage, the ejection port of the sample-gas injector is placed on a gas downstream side from an end of the collector electrode on a side where the bias electrode is located, the ejection port of the sample-gas injector is placed at a distance of 7 mm or less from the collector electrode on the gas downstream side in the gas passage, the ejection port of the sample gas injector is placed at a position on the gas downstream side of the predetermined gas from a position at which a detection sensitivity is maximized, the latter position determined by changing the position of the ejection port of the sample-gas injector in the flowing direction of the predetermined gas, and the former position being a position at which the detection sensitivity is within a range from 90 to 10% of a maximum value of the detection sensitivity.

9. A method for tuning a dielectric barrier discharge ionization detector including:

a discharge electrode;

a voltage supplier for applying AC voltage to the discharge electrode so as to generate plasma by causing a dielectric barrier discharge in a gas passage through which a predetermined gas is passed;

a sample gas injector placed on a gas downstream side from a generation area of the plasma within the gas passage, having an ejection port for ejecting a sample gas in a direction opposite to a flowing direction of the gas; and an ion detector placed on the gas downstream side from the generation area of the plasma within the gas passage, including a collector electrode for collecting ions generated from a sample component in the sample gas by light emitted from the plasma, and the method comprising:

a maximum position searching step, in which a position of the ejection port at which a detection sensitivity is maximized is searched for while a position of the ejection port in the sample gas injector is changed in the flowing direction of the predetermined gas; and an ejection port position setting step, in which the position of the ejection port of the sample gas injector is set at a position which is on the gas downstream side of the predetermined gas from the position of the ejection port located in the maximum position searching step and at which a detection sensitivity within a range from 90 to 10% of a maximum value of the detection sensitivity is obtained.

* * * * *